(12) United States Patent
Walukas et al.

(10) Patent No.: US 9,977,003 B2
(45) Date of Patent: *May 22, 2018

(54) NON-CONTACT EGG IDENTIFICATION SYSTEM FOR DETERMINING EGG VIABILITY USING TRANSMISSION SPECTROSCOPY, AND ASSOCIATED METHOD

(71) Applicant: Zoetis Services LLC, Parsippany, NJ (US)

(72) Inventors: Joel James Walukas, Cary, NC (US); Ramin Karimpour, Raleigh, NC (US)

(73) Assignee: Zoetis Services LLC, Parsippany, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/341,075

(22) Filed: Nov. 2, 2016

(65) Prior Publication Data
US 2017/0052163 A1    Feb. 23, 2017

Related U.S. Application Data

(63) Continuation of application No. 14/536,869, filed on Nov. 10, 2014, now Pat. No. 9,513,270.
(Continued)

(51) Int. Cl.
*G01N 33/08* (2006.01)
*G01N 21/3563* (2014.01)
(Continued)

(52) U.S. Cl.
CPC ........... *G01N 33/085* (2013.01); *A01K 43/00* (2013.01); *G01N 21/255* (2013.01);
(Continued)

(58) Field of Classification Search
CPC ...... G01N 33/08; G01N 21/59; G01N 33/085; G01N 21/3563; G01N 2201/125;
(Continued)

(56) References Cited

U.S. PATENT DOCUMENTS 3,540,824 A    11/1970  Fonda et al.
4,017,192 A     4/1977  Rosenthal
(Continued)

FOREIGN PATENT DOCUMENTS

FR    2455282 A1    11/1980
JP    09127096 A     5/1997
(Continued)

OTHER PUBLICATIONS

Hirota et al., "Optical Studies of Excitation-Contraction Coupling in the Early Embryonic Chick Heart," J. Physiol., 1985, vol. 366, pp. 89-106.
(Continued)

*Primary Examiner* — Michael P Lapage
(74) *Attorney, Agent, or Firm* — Scott C. Mayhew

(57) ABSTRACT

An egg identification system for determining viability of an avian egg is provided. Such a system includes an emitter assembly configured to emit electromagnetic radiation toward an egg. A detector assembly is axially aligned with the emitter assembly to detect electromagnetic radiation transmitted through the egg. The detector assembly is spaced-apart from the egg during operation thereof such that the detector assembly does not contact the egg. The detected electromagnetic radiation is processed using transmission spectroscopy analysis to determine whether the egg is viable. An associated method is also provided.

14 Claims, 10 Drawing Sheets

Related U.S. Application Data

(60) Provisional application No. 61/905,401, filed on Nov. 18, 2013.

(51) Int. Cl.
  *G01N 21/25* (2006.01)
  *G01N 21/64* (2006.01)
  *A01K 43/00* (2006.01)

(52) U.S. Cl.
  CPC ....... *G01N 21/3563* (2013.01); *G01N 21/645* (2013.01); *G01N 21/6486* (2013.01); *G01N 2021/6417* (2013.01); *G01N 2021/6491* (2013.01); *G01N 2201/0438* (2013.01); *G01N 2201/061* (2013.01)

(58) Field of Classification Search
  CPC ................ G01N 2201/62; A61B 5/704; A61B 2503/40; A01K 45/007; A01K 43/00
  See application file for complete search history.

(56) References Cited

U.S. PATENT DOCUMENTS

| | | | |
|---|---|---|---|
| 4,037,151 A | 7/1977 | Takeuchi | |
| 4,039,259 A | 8/1977 | Saito et al. | |
| 4,063,822 A * | 12/1977 | deJong | G01N 33/085 356/325 |
| 4,671,652 A * | 6/1987 | van Asselt | G01N 33/085 356/53 |
| 4,914,672 A * | 4/1990 | Hebrank | G01N 33/08 209/510 |
| 4,955,728 A | 9/1990 | Hebrank | |
| 5,173,737 A | 12/1992 | Mitchell et al. | |
| 5,504,572 A | 4/1996 | Taylor et al. | |
| 5,745,228 A * | 4/1998 | Hebrank | G01N 33/085 250/341.1 |
| 5,853,372 A | 12/1998 | Britton | |
| 6,234,320 B1 | 5/2001 | Hebrank | |
| 6,488,156 B1 | 12/2002 | Cohen | |
| 6,535,277 B2 | 3/2003 | Chalker, II et al. | |
| 6,750,954 B2 * | 6/2004 | Hebrank | A01K 43/00 356/53 |
| 6,860,225 B2 | 3/2005 | Hebrank | |
| 7,154,594 B2 | 12/2006 | Reeves et al. | |
| 7,289,196 B2 | 10/2007 | Reeves et al. | |
| 8,107,060 B2 | 1/2012 | Hebrank et al. | |
| 2002/0075476 A1 | 6/2002 | Chalker, II et al. | |
| 2002/0157613 A1 * | 10/2002 | Phelps | A01K 45/00 119/6.8 |
| 2003/0062422 A1 * | 4/2003 | Fateley | G06K 19/06 235/494 |
| 2003/0156273 A1 * | 8/2003 | Kageyama | G01N 33/085 356/52 |
| 2003/0227613 A1 * | 12/2003 | Hebrank | C12N 7/00 356/52 |
| 2004/0065263 A1 | 4/2004 | Hebrank et al. | |
| 2007/0024843 A1 * | 2/2007 | Hebrank | G01N 33/08 356/53 |
| 2012/0058052 A1 * | 3/2012 | Decuypere | A01K 45/00 424/9.6 |

FOREIGN PATENT DOCUMENTS

| | | |
|---|---|---|
| JP | 2001041882 A2 | 2/2001 |
| JP | 2013242190 A2 | 12/2013 |
| JP | 2014153333 A2 | 8/2014 |
| SU | 1597173 A1 | 10/1990 |
| WO | WO 98/14781 A1 | 4/1998 |

OTHER PUBLICATIONS

Lewin et al., "Pulse oximetry: a new way of determining the heart rate in chicken embryos," 1997, Eur. J. Physiol., vol. 434, pp. 639-641.

Romdhane Karoui et al., 2006, "Development of a rapid method based on front face fluorescence spectroscopy for the monitoring of egg freshness: 1-evolution of thick and thin egg albumens", European Food Research and Technology, vol. 223, pp. 303-312.

PCT International Search Report and the Written Opinion, International Application No. PCT/US2014/066026, dated Feb. 4, 2015.

\* cited by examiner

NON-CONTACT EGG IDENTIFICATION SYSTEM FOR DETERMINING EGG VIABILITY USING TRANSMISSION SPECTROSCOPY, AND ASSOCIATED METHOD

CROSS REFERENCE TO RELATED APPLICATIONS

This application is a continuation of U.S. application Ser. No. 14/536,869, filed Nov. 10, 2014, which claims the benefit under 35 U.S.C. § 119(e) of U.S. Provisional Patent Application No. 61/905,401, filed Nov. 18, 2013, both of which are expressly incorporated herein by reference in their entirety.

TECHNICAL FIELD

The present disclosure generally relates to egg identification systems. More particularly, the present disclosure relates to a non-contact egg identification system capable of determining whether a viable embryo is present within an avian egg by using transmission spectroscopy, and an associated method.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to herein as "non-live eggs"). Non-live eggs (also referred to as non-viable eggs) are removed from incubation to increase available incubator space. In many instances it is desirable to introduce a substance, via in ovo injection, into a live egg (also referred to as a viable egg) prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. Such devices may position an egg and an injection needle in a fixed relationship to each other, and may be designed for the high-speed automated injection of a plurality of eggs. The selection of both the site and time of injection treatment can also impact the effectiveness of the injected substance, as well as the mortality rate of the injected eggs or treated embryos.

In commercial poultry production, only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the use of automated methods for in ovo injection, and the cost of treatment substances, an automated method for identifying live eggs and selectively injecting (or selectively contacting) only live eggs, is desirable.

An egg may be a "live" egg, meaning that it has a viable embryo. FIG. 1 illustrates a live poultry egg 1 at about day one of incubation. FIG. 2 illustrates the live egg 1 at about day eleven of incubation. The egg 1 has a somewhat narrow end in the vicinity represented at 10 as well as an oppositely disposed broadened or blunt end portion in the vicinity shown at 20. In FIG. 1, an embryo 2 is represented atop the yolk 3. The egg 1 contains an air cell 4 adjacent the broadened end 20. As illustrated in FIG. 2, the wings 5, legs 6, and beak 7 of a baby chick have developed.

An egg may be a "clear" or "infertile" egg, meaning that it does not have an embryo. More particularly, a "clear" egg is an infertile egg that has not rotted. An egg may be an "early dead" egg, meaning that it has an embryo which died at about one to five days old. An egg may be a "mid-dead" egg, meaning that it has an embryo which died at about five to fifteen days old. An egg may be a "late-dead" egg, meaning that it has an embryo which died at about fifteen to eighteen days old.

An egg may be a "rotted" egg, meaning that the egg includes a rotted infertile yolk (for example, as a result of a crack in the egg's shell) or, alternatively, a rotted, dead embryo. While an "early dead," "mid-dead" or "late-dead egg" may be a rotted egg, those terms as used herein refer to such eggs which have not rotted. Clear, early-dead, mid-dead, late-dead, and rotted eggs may also be categorized as "non-live" eggs because they do not include a living embryo.

There are other applications where it is important to be able to distinguish between live (viable) and non-live (non-viable) eggs. One of these applications is the cultivation and harvesting of vaccines via live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the agnostic fluid from the egg. Typically, eggs are candled before injection of a seed virus to remove non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

Some previous candling apparatuses have employed opacity identification systems in which a plurality of light sources and corresponding light detectors are mounted in an array, and wherein eggs are passed on a flat between the light sources and the light detectors. Unfortunately, such conventional candling techniques may have somewhat limited accuracy, especially at high candling through-put speeds. Pulsed light opacity identification systems can operate at speeds equivalent to about 300,000 eggs per hour and successfully identify clear eggs from a stream of eggs. However, some eggs identified as being live will in fact be non-live (e.g., rotted eggs, mid and late dead eggs).

Other previous candling apparatuses have employed spectroscopy detection modes capable of determining live and non-live eggs. Unfortunately, these systems require the detection tooling to contact the eggs in order to create a mechanical light seal for detection purposes, which may present several problems. First, the throughput parameter is slowed down because the eggs must be stopped while the detection tooling head is lowered and raised in order for each detection tooling to contact a respective egg. Next, mechanical contact with the non-live eggs, particularly with the rotted eggs (which can explode when contacted), may undesirably introduce contamination into the detection system or the surrounding area/eggs, which could potentially be transferred to subsequent live eggs during further processing. Finally, the emitter-detector configurations in previous spectroscopy detection systems are difficult to position mechanically to allow for desired throughput. In this regard, the emitter-detector configurations have been arranged to operate in a reflectance mode.

Accordingly, it would be desirable to provide a candling apparatus implementing a spectroscopic detection system capable of accurately distinguishing live and non-live eggs without making contact therewith during operation and without the use of a mechanical light seal. Furthermore, it would be desirable to provide an associated method that would facilitate spectroscopy detection of live eggs in a high throughput and accurate manner.

BRIEF SUMMARY

The above and other needs are met by aspects of the present disclosure which, according to one aspect, provides an egg identification system for determining viability of an avian egg. The system includes a conveyor system configured to convey an egg flat containing a plurality of eggs. An emitter assembly is configured to emit electromagnetic radiation toward one of the eggs conveyed in the egg flat. A non-contact detector assembly is axially aligned with the emitter assembly. The non-contact detector assembly is configured to detect the electromagnetic radiation transmitted through the egg. The non-contact detector assembly is disposed in a non-contact position such that the egg positioned for identification is spaced-apart from the non-contact detector assembly during operation thereof. A processor is configured to process an output signal of the non-contact detector assembly in a transmission spectroscopy mode for determining whether the egg is viable.

Another aspect provides a method of determining viability of an egg. The method comprises conveying an egg contained in an egg flat using a conveyor system. The method further comprises emitting electromagnetic radiation from an emitter assembly toward the egg. The method further comprises receiving electromagnetic radiation transmitted through the egg at a non-contact detector assembly axially aligned with the emitter assembly, the non-contact detector assembly being spaced-apart from the egg. The method further comprises processing an output signal of the non-contact detector assembly in a transmission spectroscopy mode for determining whether the egg is viable.

Thus, various aspects of the present disclosure provide advantages, as otherwise detailed herein.

BRIEF DESCRIPTION OF THE DRAWINGS

Figure 1:
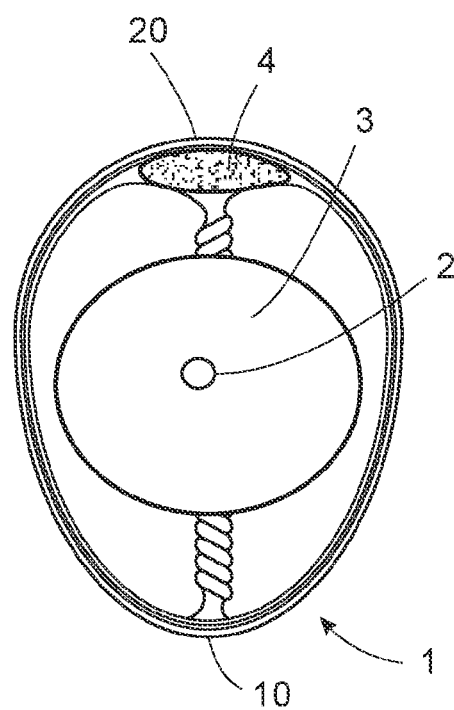
Figure 2:
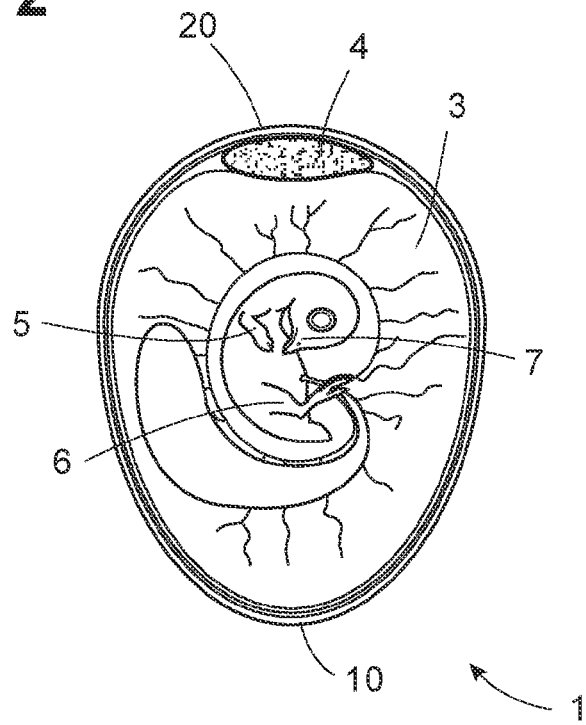
Figure 3:
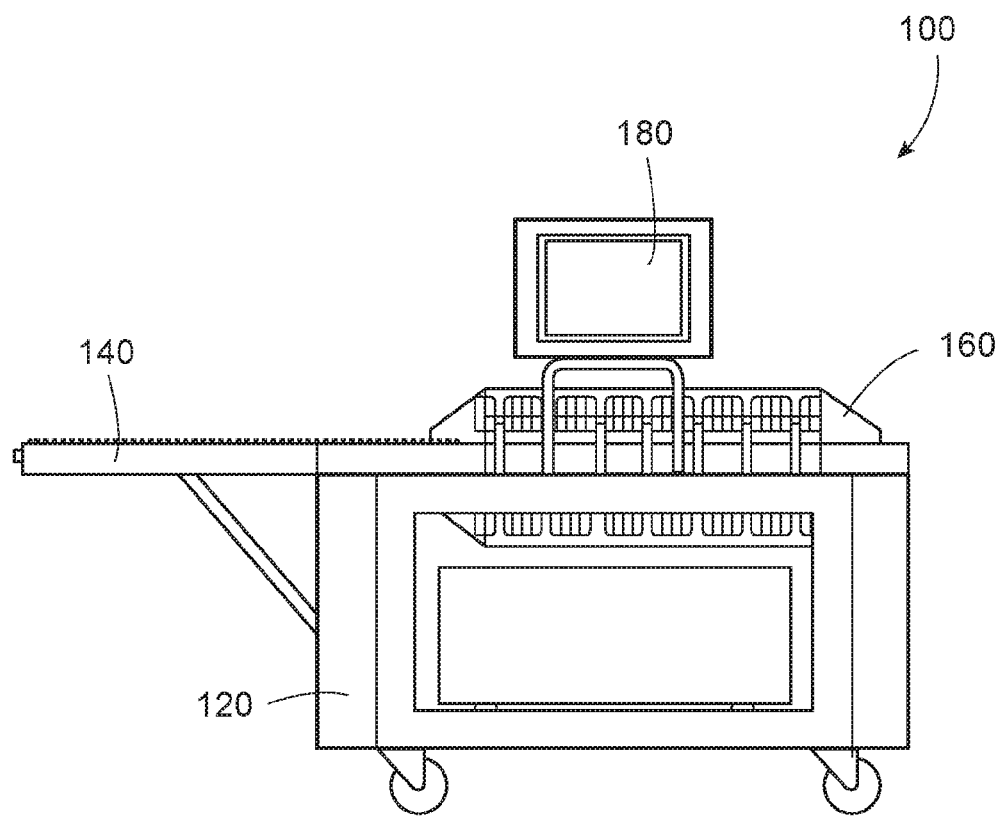
Figure 4:
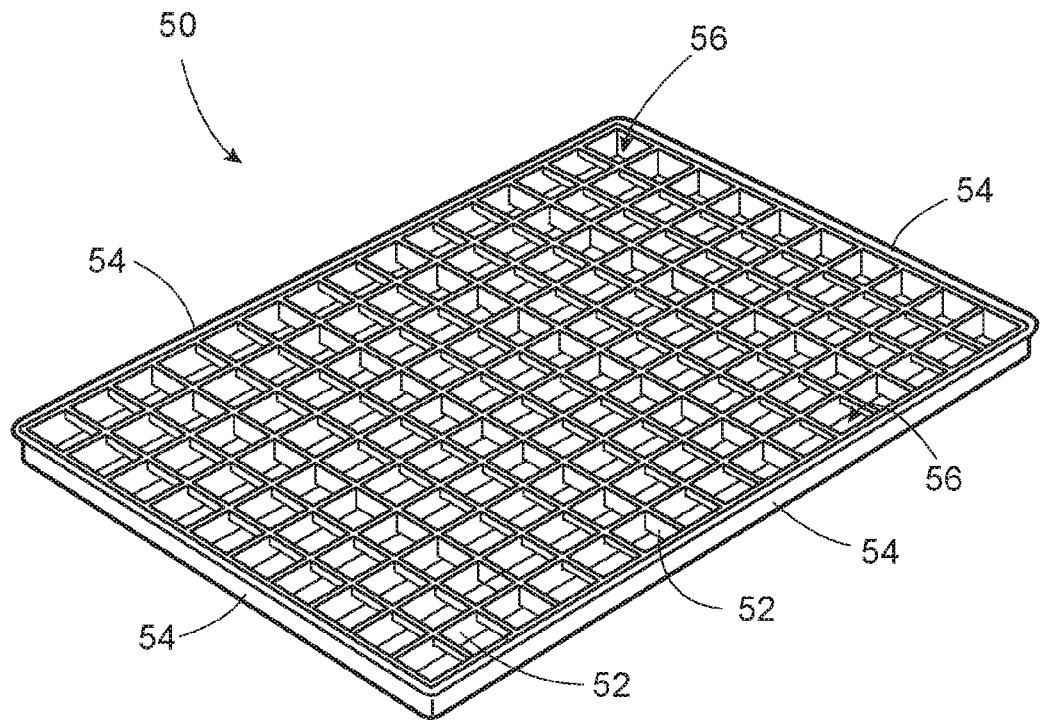
Figure 5:
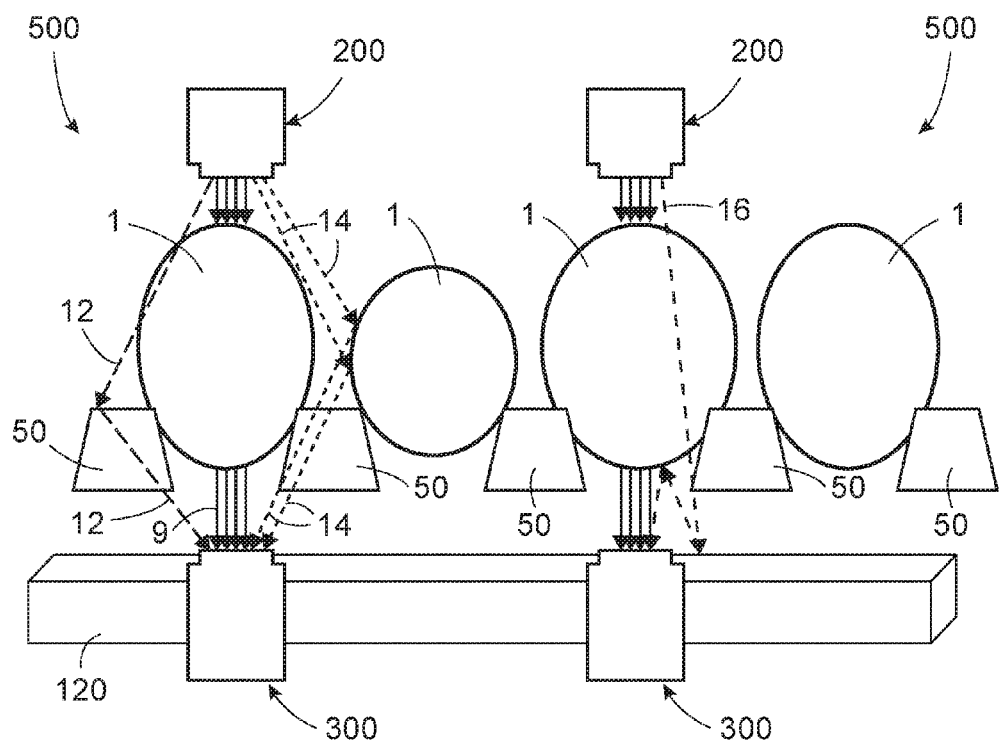
Figure 6:
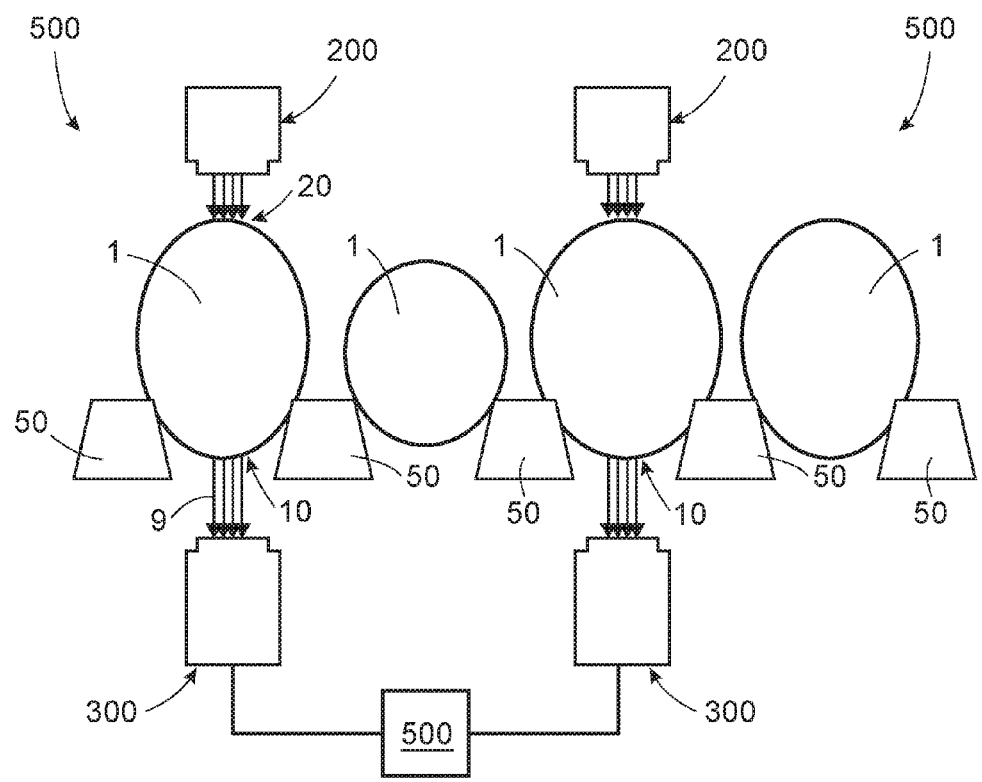
Figure 7:
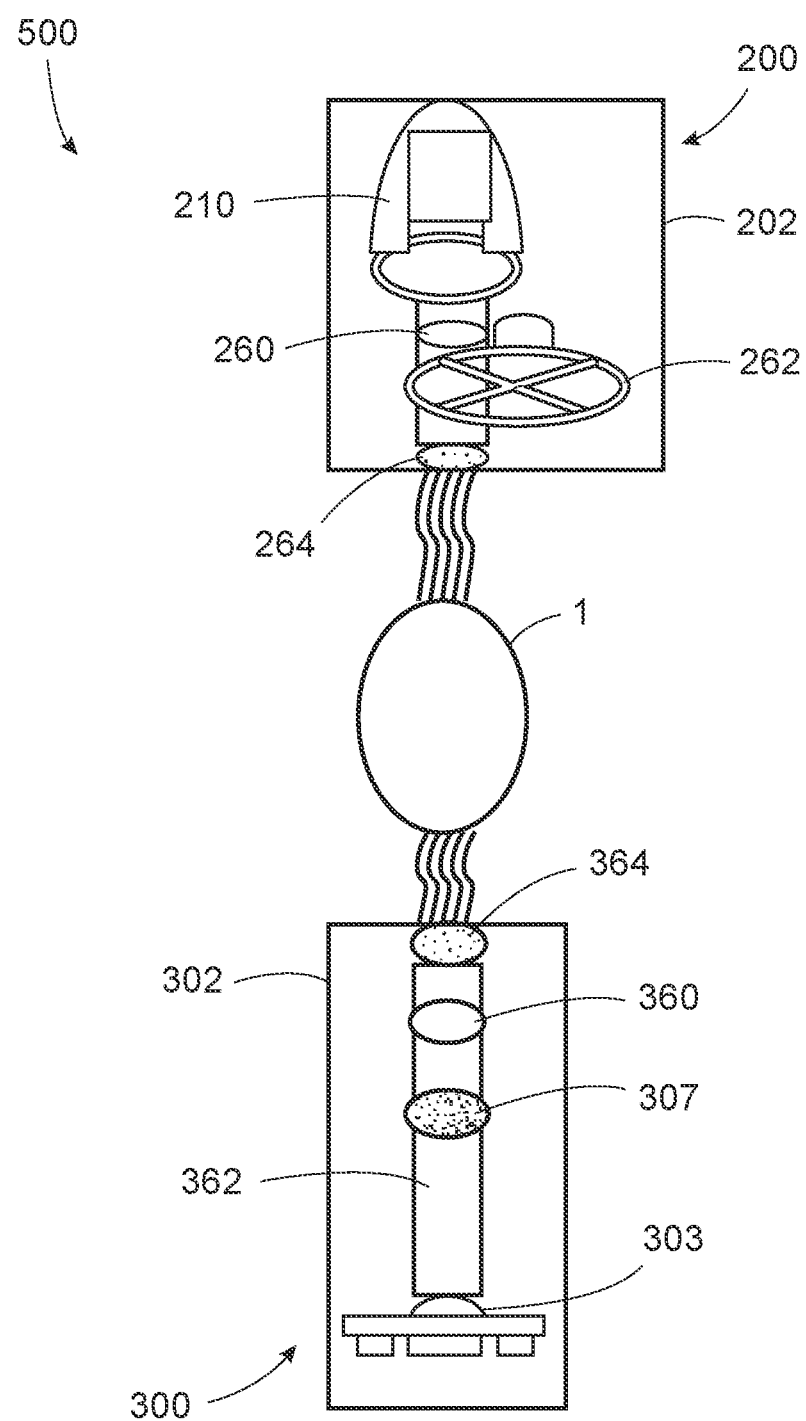
Figure 8:
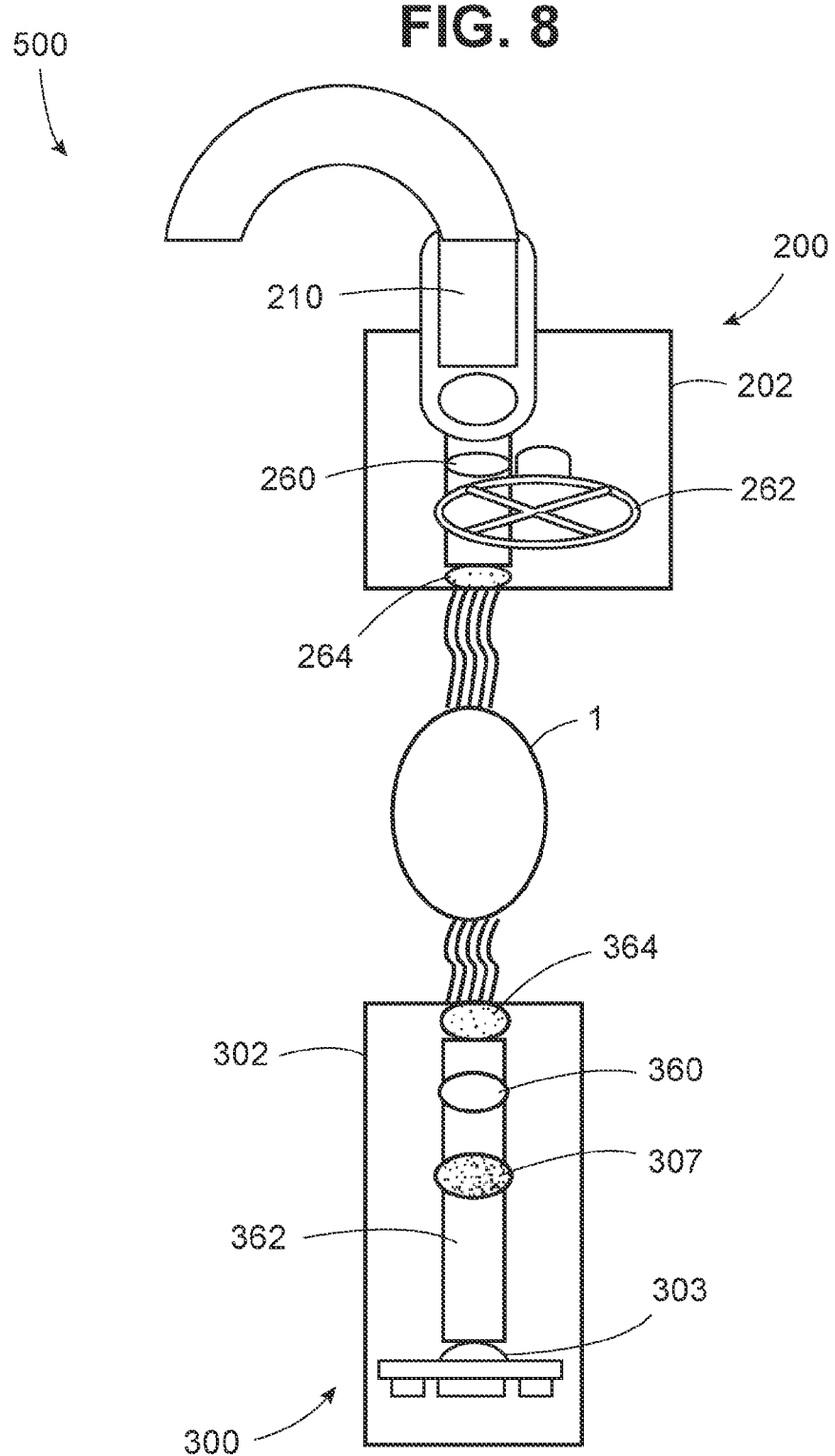
Figure 9:
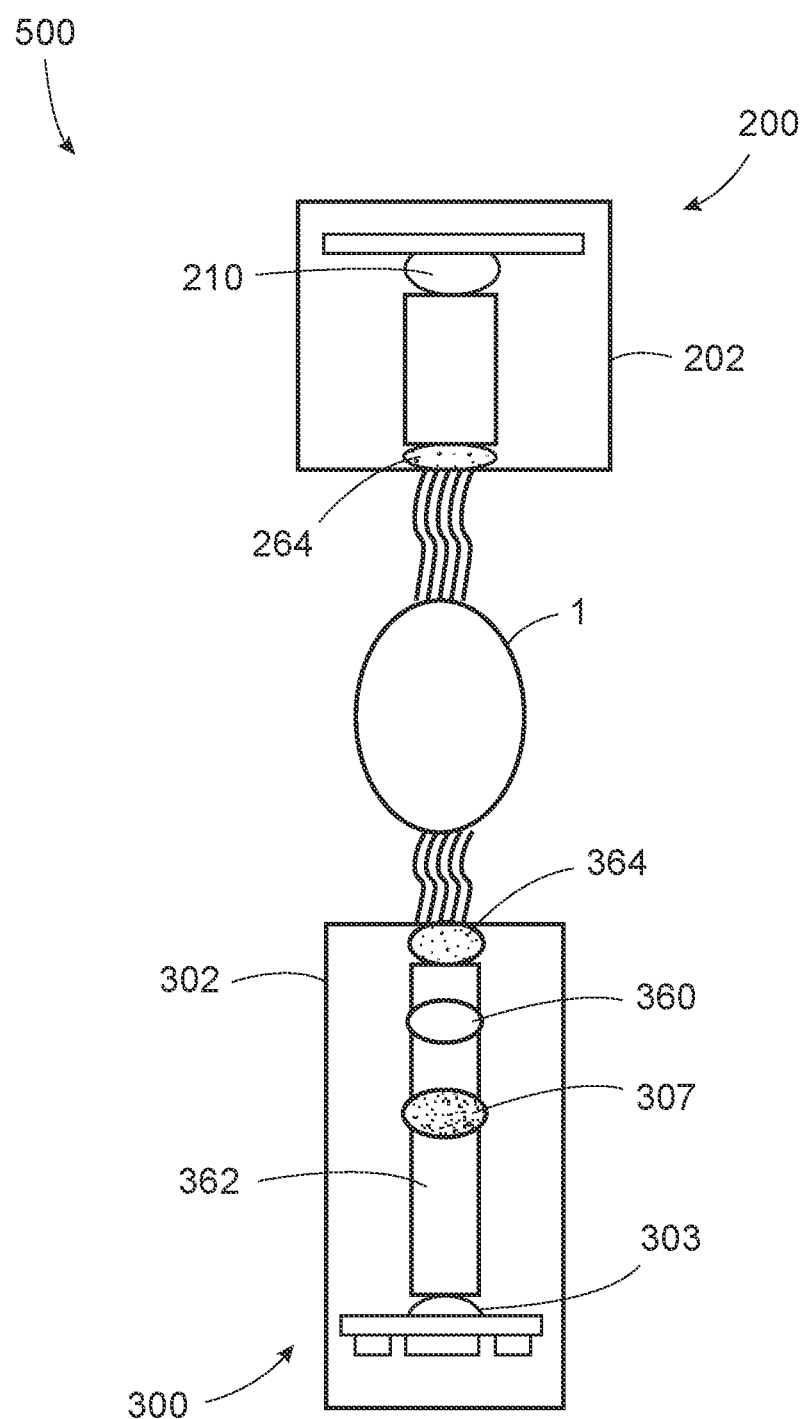
Figure 10:
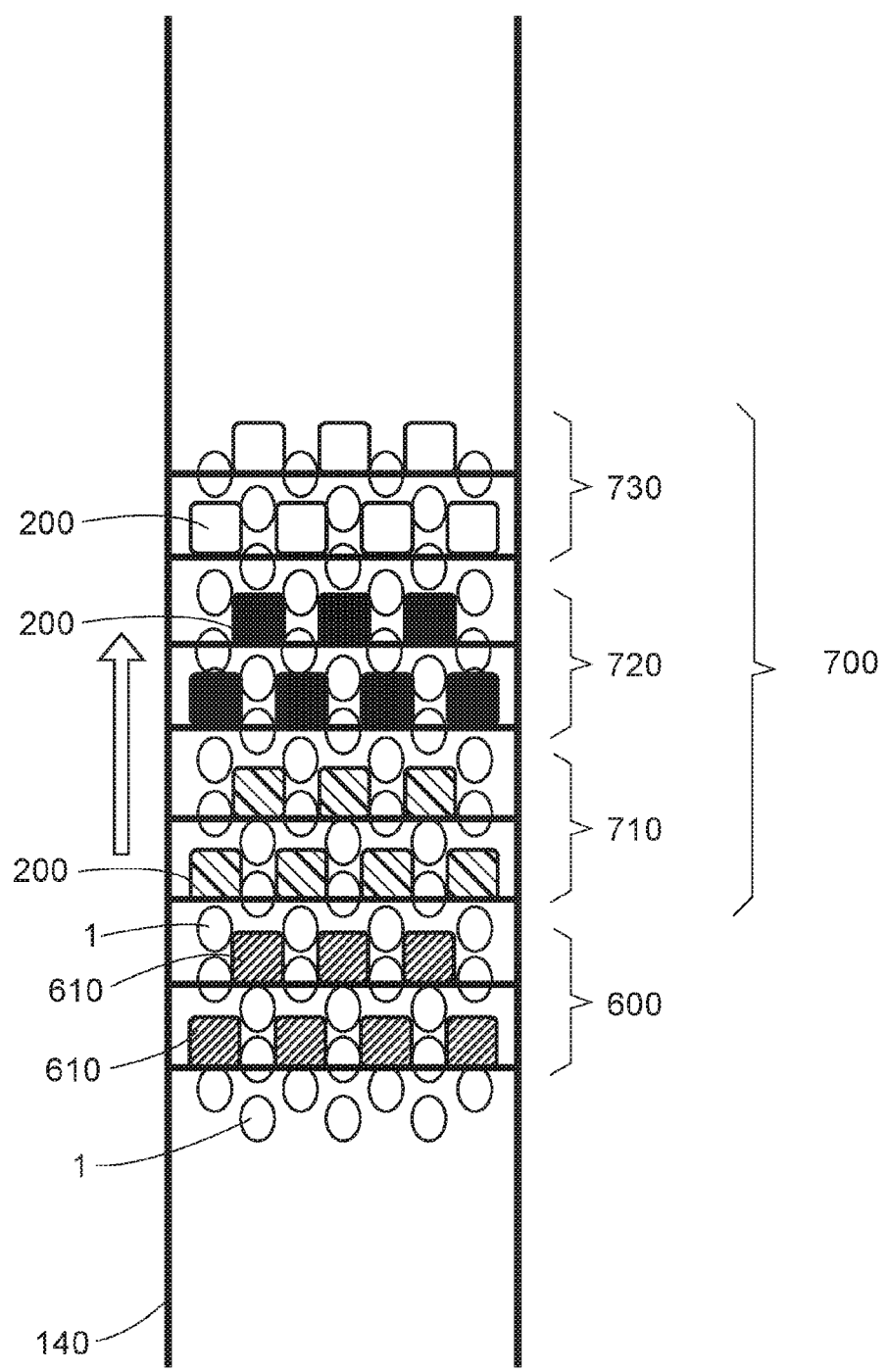
Figure 11:
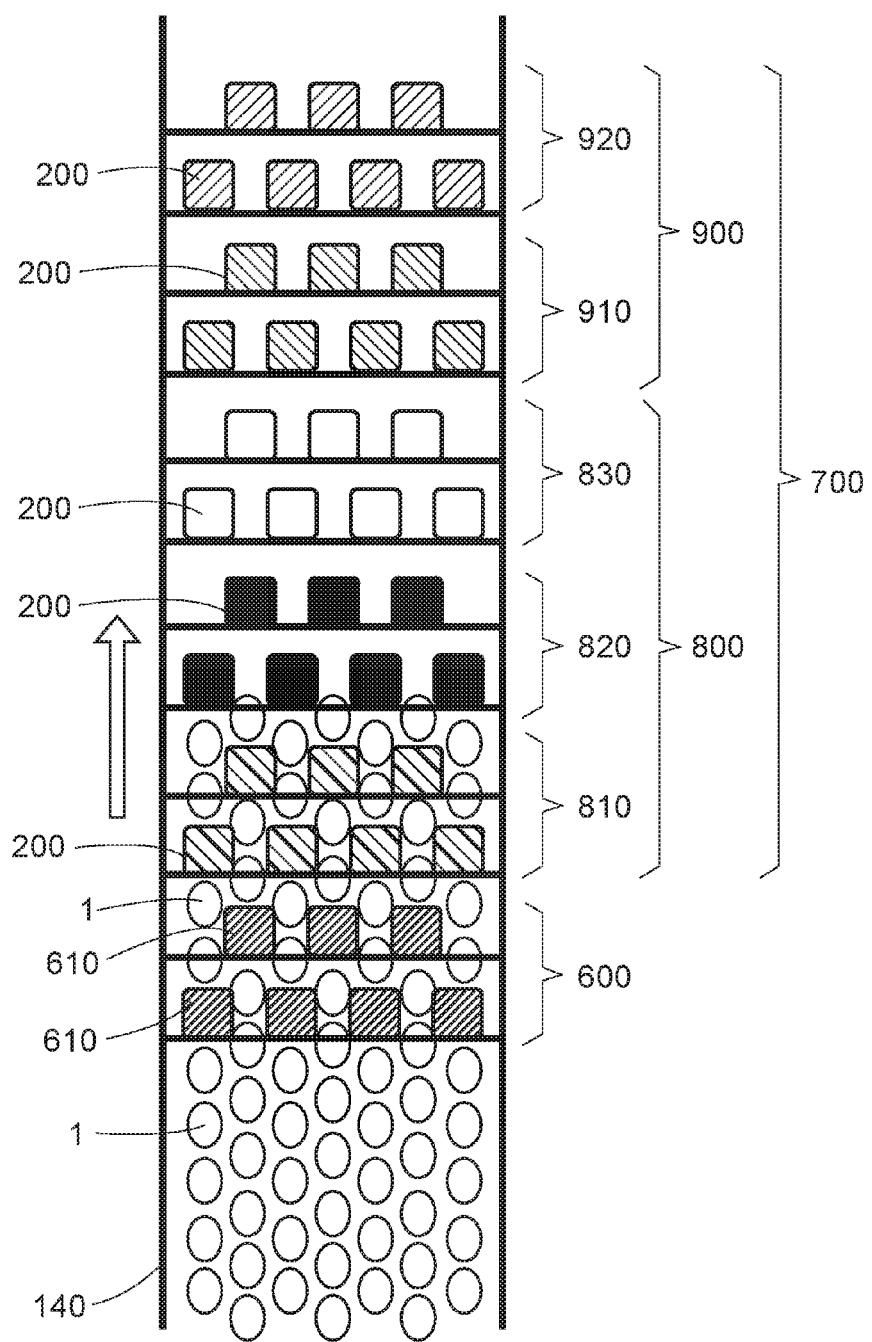

Having thus described various embodiments of the present disclosure in general terms, reference will now be made to the accompanying drawings, which are not necessarily drawn to scale, and wherein:

FIG. 1 illustrates a live chicken egg at about day one of incubation;

FIG. 2 illustrates a live chicken egg at about day eleven of incubation;

FIG. 3 is a schematic view of an egg identification system, according to one aspect of the present disclosure;

FIG. 4 is a perspective schematic view of an egg flat capable of containing eggs in a fixed position;

FIG. 5 illustrates eggs in an egg flat being conveyed past a series of emitter-detector pairs of an egg detection system, and further illustrating paths of interfering off-axis emissions that undesirably contribute to a detected signal;

FIG. 6 illustrates a plurality of eggs in an egg flat being conveyed past a series of emitter-detector pairs of an egg detection system, with limited interfering emissions contributing to a detected signal, according to one aspect of the present disclosure;

FIG. 7 illustrates an emitter-detector pair capable of use in an egg detection system, according to one aspect of the present disclosure;

FIG. 8 illustrates an emitter-detector pair capable of use in an egg detection system, according to another aspect of the present disclosure;

FIG. 9 illustrates an emitter-detector pair capable of use in an egg detection system, according to yet another aspect of the present disclosure;

FIG. 10 illustrates a plurality of eggs being conveyed through an egg detection system having an opacity detection component and a spectroscopy detection component, according to one aspect of the present disclosure; and FIG. 11 illustrates a plurality of eggs being conveyed through an egg detection system having multiple detection systems operating under various spectroscopy modes, according to one aspect of the present disclosure.

DETAILED DESCRIPTION OF THE DISCLOSURE

Various aspects of the present disclosure now will be described more fully hereinafter with reference to the accompanying drawings, in which some, but not all aspects of the disclosure are shown. Indeed, this disclosure may be embodied in many different forms and should not be construed as limited to the aspects set forth herein; rather, these aspects are provided so that this disclosure will satisfy applicable legal requirements. Like numbers refer to like elements throughout.

The present disclosure is directed to systems and methods for accurately determining the viability of a plurality of eggs in a high throughput manner without contacting the eggs as the eggs pass through an identification means. Passing of the eggs through the system in a non-contact or contactless manner provides many advantages, including maintaining stationary position of the detection system components to improve throughput and limiting contact with non-live eggs such as rotted eggs that may explode.

As used herein, the terms "non-contact" and "contactless" refer to maintaining a spaced-apart relationship between the egg and certain components of the egg identification system disclosed herein during operation of the emitter-detector pairs when determining viability. In some instances, this may specifically refer to the spaced-apart relationship of the detector assembly to the egg. In this regard, the detector assembly of the present disclosure may be positioned apart from the egg such that no component thereof contacts the egg, thereby eliminating any mechanical light seal capable of limiting interference signals from being detected. Instead, the present disclosure addresses these interference signals by other means in such a manner that contact with the egg is not required. Of course, the eggs may be in contact with a carrier means, such as an egg flat, configured to transport the eggs through the egg identification system. In this regard, the term "non-contact" refers to the avoidance of contact between the eggs and the operating components of the egg identification system.

Furthermore, the present disclosure is directed to systems and methods using transmission (so-called "through beam") modes for determining viability of an egg. By operating in a transmission mode, the emitter and detector of the egg identification system may be axially aligned along a common longitudinal axis such that the system may be configured in a workable manner. That is, the system configuration doesn't have to account for an emitter-detector pair operating in a reflectance mode and having an emitter and detector arranged, for example, at right angles for receiving a reflectance signal. Instead, the emitter assembly and the detector assembly may be positioned on opposite sides of the eggs such that the eggs can easily pass therebetween for evaluation and identification.

However, because aspects of the present disclosure may operate in a non-contact and transmission manner, the desired transmitted light levels may be low while the potential for undesirable interference signals may be high. In this regard, further aspects of the present disclosure are provided such that the undesired interference signals may be limited and the desired low transmission signal (less than about 1 nW/cm$^2$) may be maximized for processing so as to provide accurate and reliable identification of viable eggs.

The methods and systems according to aspects of the present disclosure may be utilized for accurately identifying live and non-live eggs at any time during embryonic development (also referred to as the incubation period). Aspects of the present disclosure are not limited to identification only at a particular day (e.g., day eleven) or time period during the embryonic development period. In addition, methods and apparatus according to aspects of the present disclosure may be used with any types of avian eggs including, but not limited to, chicken, turkey, duck, geese, quail, pheasant eggs, exotic bird eggs, etc.

FIG. 3 illustrates an egg identification system 100 capable of implementing various aspects of the present disclosure. The egg identification system 100 may include a frame 120 and a conveyor system 140 configured to convey a plurality of eggs contained in an egg flat 50 (FIG. 4) to an egg detection system 160. In some instances, the egg identification system may include a display 180 capable of displaying information related to the egg identification system and/or the eggs passing through the egg detection system 160 for identification thereof. The egg identification system 100 may include a controller for controlling various aspects of thereof, including the ability to enable and disable certain components of the egg detection system 160. The egg identification system 100 may be portable and, in some instances, may be configured in a modular manner such that it may be connected to other associated devices, such as, for example, an egg injection apparatus, an egg sorting apparatus, an egg transfer apparatus, an egg remover apparatus, or a gender identification apparatus. In some instances, the egg detection system 160 may be directly applied to an egg injection apparatus, an egg sorting apparatus, an egg transfer apparatus, an egg remover apparatus, or a gender identification apparatus.

Referring to FIG. 4, the egg flat 50 may be formed of a plurality of intersecting slats 52 confined by a plurality of ends 54. The slats 52 may define a plurality of open-ended pockets 56, with each pocket 56 capable of receiving an end of a respective egg 1. In some instances, the narrow end 10 (FIGS. 1 and 2) of the egg 1 may be received within the pocket 56 such that the blunt end 20 projects above the egg flat 50. Although eggs may be carried in egg flats 50, any means of presenting a plurality of eggs over time to the egg detection system 160 for identifying the present condition of eggs may be used.

Referring now to FIG. 6, the egg detection system 160 for non-invasively identifying viability of an egg, according to aspects of the present disclosure, is illustrated schematically. An egg 1 may be illuminated with light from a light emission source 210 of an emitter assembly 200 positioned adjacent an egg 1 at the blunt end 20 thereof. In some instances, the light emitted from the light emission source 210 may be collimated. Each egg may be illuminated with light at wavelengths of anywhere between about 400 and 2600 nanometers, and particularly within the visible spectrum, the infrared spectrum, the near-infrared spectrum, or the ultraviolet spectrum. A detector assembly 300 may be positioned adjacent the narrow end 10 of the egg 1, opposite the emitter assembly 200, and may receive light transmitted through the egg. The detector assembly 300 may further include a spectrometer 302 for determining the irradiance of the received light for selected wavelengths of light. The spectrometer 302 may be configured to measure the intensity of radiation absorbed, reflected, or emitted by a material as a function of wavelength.

The particular aspects of interest of the received light may be determined at selected wavelengths. A spectrum that represents light intensity at selected wavelengths may be generated. A spectrum may be subjected to various processing algorithms that are based upon calibrated spectra. The generated spectrum may then be compared with at least one spectrum, wherein each spectrum is associated with a respective known egg condition, to identify viability of the egg. For example, the spectrum for an egg in question may be compared with a spectrum associated with the following types of eggs: fertile eggs, live eggs, early dead eggs, middle dead eggs, late dead eggs, clear eggs, cracked eggs, rotted eggs, or missing eggs. This comparison may involve processing a spectrum via an analytical model (consisting of one or more algorithms) which is built from known spectra. The outputs of an analytical model may be designed to correspond with specific types of eggs.

Spectrum processing may involve adjusting a spectrum (either by selective scaling and/or shifting) based upon factors derived from calibration spectra obtained from reference eggs. This may allow spectra produced by different detector assemblies 300 and at different times to be objectively compared. Additional processing of a spectrum before comparison with a reference spectrum may involve noise reduction.

The spectrometer 302 may be configured (e.g., via a microprocessor) to convert light intensity values for an egg 1 into a spectrum. In addition, the spectrometer 302 may be configured to compare a generated spectrum for an egg with at least one spectrum associated with a known egg condition to identify a present condition (i.e., viability or non-viability) of the egg 1. For example, a generated spectrum may be compared with a spectrum of an egg known to be live in order to determine whether the egg in question is a live egg. Similarly, comparisons with spectra associated with known conditions may be made to determine whether an egg in question is early dead, middle dead, late dead, clear, cracked, rotted, and/or missing.

The egg identification system 100 may include a controller operatively connected to the spectrometer 302. The controller may control the light emission source 210 and may receive and process signals from the spectrometer 302.

The controller may also compare a spectrum generated for an egg with a plurality of spectra associated with known egg conditions and, using this comparison data, may classify an egg according to type (i.e., live, clear, dead, rotted). An operator interface (e.g., a display) 180 may be preferably provided to allow an operator to interact with the controller.

The controller may be configured to: 1) generate control signals to actuate and deactuate one or more light emission sources 210; 2) receive and process signals from the spectrometer 302; and 3) process and store data associated with each egg. The controller may include a processor 500 or other suitable programmable or non-programmable circuitry including suitable software. The controller may also include such other devices as appropriate to control the one or more light emission sources 210 and spectrometer 302, process or otherwise assess and evaluate signals from the spectrometer 302.

The operator interface 180 may be any suitable user interface device and preferably includes a touch screen or keyboard. The operator interface 180 may allow the user to retrieve various information from the controller, to set various parameters and/or to program/reprogram the controller. The operator interface 180 may include other peripheral devices, for example, a printer and a connection to a computer network. The identified conditions of each of a plurality of eggs in a flat 50 may be displayed graphically via the operator interface 180 along with cumulative statistics for a group or flock of eggs. Such cumulative statistics may be assembled, calculated and/or estimated by the controller using the classification data. The cumulative statistics may include, for each group, flock or flat, early dead percentage, mid-dead percentage, and percentage of rotted eggs. These statistics may be useful to monitor and evaluate hatchery and incubator operation, and status and performance of breeds or flocks.

According to aspects of the present disclosure, the emitter-detector pairs may be configured to operate in an absorption spectroscopy mode or a fluorescence spectroscopy mode. In some instances, the emitter-detector pairs may be configured to operate in an infrared absorption spectroscopy mode. The modes of operation described herein refer to transmission spectroscopy, as opposed to reflectance spectroscopy, and particularly refer to configurations in which the emitter assembly 200 and the detector assembly 300 are axially aligned and position opposite one another such that the egg 1 passes between the emitter-detector pair.

Absorption spectroscopy refers to spectroscopic techniques that measure the absorption of radiation, as a function of frequency or wavelength, due to its interaction with a sample (e.g., an egg). In this regard, the egg absorbs energy (i.e., photons) from the radiating field. The intensity of the absorption varies as a function of frequency, and this variation is the absorption spectrum. Absorption spectroscopy may be performed across the electromagnetic spectrum. A generated beam of radiation may be directed at the egg and the intensity of the radiation that passes through the egg detected. The transmitted energy may be used to calculate the absorption. When radiation from the light emission source 210 occurs within wavelengths of the infrared spectrum, the technique is referred to as infrared absorption spectroscopy.

Fluorescence spectroscopy refers to a type of electromagnetic spectroscopy that analyzes fluorescence from a sample. Fluorescence spectroscopy involves using a beam of light to excite electrons in molecules of certain compounds and causes them to emit light, which in some instances may be visible light, but may also be light in the infrared, near-infrared, or ultraviolet spectrums. Spectrometers used in fluorescence spectroscopy may be referred to as fluorometers or fluorimeters. In some instances, the different wavelengths of fluorescent light emitted by a sample are measured, wherein in some instances the excitation light is held at a constant wavelength, which is an emission spectrum. An excitation spectrum is the opposite, whereby the emission light is held at a constant wavelength, and the excitation light is scanned through many different wavelengths. In some instances, an emission map is measured by recording the emission spectra resulting from a range of excitation wavelengths and combining them all together. This presents a three dimensional surface data set that may be depicted as a contour map. In some instances, a multispectral analysis may be implemented to determine a signature for eggs having a certain condition. According to some aspects, the detector assembly 300 may be tuned to only respond to a predetermined fluorescence wavelength, while stray light with wavelengths differing from the predetermined fluorescence wavelength being ignored by the electronics of the detector assembly 300.

According to some aspects of the present disclosure, with respect to transmission fluorescence spectroscopy, the combination of intensity sorting at one wavelength and ratio sorting using two excitation wavelengths, such as, for example, about 650 nanometers and about 720 nanometers using an emission filter at about 830 nanometers may provide a high-level of accuracy.

Referring now to FIGS. 5 and 6, an emitter-detector pair 500 for use in classifying eggs, according to some aspects of the present disclosure, is illustrated. The illustrated emitter-detector pair 500 may include an emitter assembly 200 and a detector assembly 300. In operation, a plurality of the emitter-detector pairs 500 may be arranged in an array and utilized to classify a respective array of eggs supported by an egg flat 50 (FIG. 4). The illustrated emitter assembly 200 may include a cylindrical emitter housing 202. Aspects of the present disclosure are not limited to the illustrated configuration of the emitter housing 202. The emitter housing 202 may have various shapes, sizes and configurations without limitation. An array of the emitter assemblies 200 may be supported via a frame or other supporting member of the egg detection system 160. Because the egg detection system 160 operates in a non-contact manner, the emitter assemblies 200 may not need to move between a raised position and a lowered position, although in some instances each may be configured for such.

FIG. 5 illustrates the various potential emission paths that the electromagnetic radiation emitted by the light emission source 210 may travel when exiting the emitter assembly 200. As mentioned previously, detecting the low transmitted light levels 9 transmitted through the egg 1 without the use of a mechanical light seal provides a challenge when evaluating viability of the egg 1 based upon spectroscopy. In light of the absence of mechanical light seals, aspects of the present disclosure may be configured to minimize the generation of interfering reflective signals such as light 12 reflected through the egg flat 50, light 14 reflected from adjacent eggs, and light 16 reflected from the frame 120 and other associated components.

The emitter assembly 200 may be configured to maximize emission of the electromagnetic radiation along a longitudinal axis of the egg 1 such that the emissions are coherently directed toward the egg 1, while also maximizing rejection of off-axis emissions. That is, the emitter assembly 200 may be configured to project the emission of the light emission source 210 onto a prescribed region of the egg 1, while limiting the emission of stray light, wherein stray light is any optical energy leaving the emitter assembly 200 that does not illuminate the prescribed region of the egg.

Disposed within the emitter housing 202 is a light emission source 210. The light emission source 210 may be configured to emit electromagnetic radiation of various wavelengths of the electromagnetic spectrum, including, for example, visible light, infrared light and ultraviolet light. In some instances, the light emission source 210 may be particularly configured to emit light in the wavelength range of about 400 nm to 2600 nm. According to some aspects, the light emission source 210 may be formed of, for example, a light emitting diode (LED) 280 (FIG. 9), a fiber optic light source 285 (FIG. 8), or quartz tungsten halogen light source 290 (FIG. 7) configured to emit light from various portions of the electromagnetic spectrum. However, aspects of the present disclosure are not limited to the use of LEDs or infrared radiation. Various types of light emission sources may be utilized without limitation. In particular, any solid state excitation source may be utilized.

According to some aspects, as shown in FIGS. 7-9, the emitter assembly 200 may include an optical filter 260. In some instances, a modulation wheel 262 and associated drive assembly may be provided to modulate the light emitted from the light emission source 210. A collimation lens 264 may be provided to collimate the electromagnetic radiation emitted from the light emission source 210. A transparent protective emitter window may be incorporated into the emitter housing 202 to protect the internal components of the emitter assembly 200, while allowing emitted light to exit the emitter assembly 200.

Aspects of the present disclosure may also include a detector assembly 300 for receiving electromagnetic radiation/light transmitted through the egg during the candling operation. The detector assembly 300 may be positioned opposite the emitter assembly 200 in an axial alignment so as to form an emitter-detector pair. Thus, a plurality of emitter assemblies 200 and a respective plurality of detector assemblies 200 may form an array of emitter-detector pairs capable of evaluating a plurality of eggs transported in an egg flat.

As discussed previously, in some instances, the detector assembly 300 may be spaced-apart from the egg during the candling operation such that no part of the detector is in contact with the egg, thereby defining a non-contact position. Such a contactless configuration may allow for increased throughput and may limit contamination of subsequent eggs, as described previously. Thus, to provide a contactless feature, it may be desirable to maximize the collection of light emitted by the egg 1 from within a specified angular detector field of view, which represents the output signal, while minimizing the light collected from outside of the detector field of view.

According to some aspects, as shown in FIGS. 7-9, the detector assembly 300 may include a transparent protective detector window that may be incorporated into a detector housing 302 to protect the internal components of the detector assembly 300, while allowing transmitted light to enter the detector assembly 300. A collimation lens 364 may be provided to collect the electromagnetic radiation transmitted through the egg within the field of view of the detector assembly 300. In some instances, the detector assembly 300 may include an optical filter 360. In some instances, a light pipe 362 may be provided to reduce optical noise in the system. In some instances, an optical coupling lens 307 may be provided. Appropriate circuitry may be in communication with a sensor 303 (e.g., a photodetector) configured to generate an output signal transmitted to the processor 500.

In operation, once an egg 1 is disposed between the emitter-detector pair, the light emission source 210 may emit light directed into the egg 1. The sensor 303 may receive light that leaves the egg 5 and may generate an output signal corresponding to the intensity of the light leaving the egg 1.

The controller may include a processor 500 in communication with the detector assembly 300 and configured to process output signals from the sensor 303 to determine the viability of the egg 1. The intensity of light passing through an egg may be determined at a desired wavelength or signature wavelength, and a spectrum that represents light intensity at a selected wavelength may be generated. The generated spectrum may then be compared with one or more spectra associated with a respective known egg condition to identify a present condition of the egg. For example, the generated spectrum may be compared with a respective spectrum associated with one or more of the following: live eggs, early dead eggs, middle dead eggs, late dead eggs, clear eggs, rotted eggs, and/or missing eggs.

According to some aspects of the present disclosure, the egg detection system 160 may be capable of identify eggs according to viability while being continuously moved through the egg identification system 100. In this regard, the eggs 1 in the egg flat 50 may be capable of being continuously moved through the egg identification system 100 during viability evaluation thereof, thereby allowing for an optimal throughput as desired. To that end, the egg flat 50 does not need to be stopped during identification processing to allow for detector tools to contact the eggs 1 or otherwise be angularly positioned for detection. In some instances, however, the egg flat 50 may be stopped or paused between an emitter-detector pair for identification. In any event, the conveyor system 140 may be synchronized to convey the egg flats 50 at variable speeds.

While the blunt end 20 of the egg 1 is shown and described as being irradiated, it is possible that the positions of the emitter assembly 200 and the detector assembly 300 may be switched such that the electromagnetic radiation is directed upward into the narrow end 10 of the egg 1 and the transmitted light detected at the blunt end 20.

According to some aspects, as shown in FIGS. 10 and 11, the egg detection system 160 may include an opacity identification system 600 and a spectroscopy detection system 700. The spectroscopy detection system 700 is represented by the aspects previously described with respect to FIGS. 5-9. In some instances, the opacity identification system 600 may be provided upstream in a processing direction 800 from the spectroscopy detection system 700. The opacity identification system 600 implements optoelectronic identification and may include an emitter assembly (individual emitters 610) located above the conveyed egg flats 50 and a receiver assembly located below the conveyed egg flats 50. The opacity identification system 600 scans eggs and identifies the eggs as non-viable (clear) or viable (non-clear) before being conveyed to the spectroscopy detection system 700. Each emitter 610 may direct light down through each egg 1 and a receiver gathers the light passed through the egg. Light passing through each egg 1 may be measured to determine if the egg is non-viable or viable. The light may be emitted at an optical bandwidth of between about 720 nanometers and about 935 nanometers.

In this regard, the opacity identification system 600 may be used as a first-pass identifier to identify clear eggs, early-dead eggs, or eggs missing from the egg flat 50 before passing them through the spectroscopy detection system 700. In order to limit saturation of the detector assemblies 300 of the spectroscopy detection system 700, respective positions of the emitter-detector pairs may be turned-off, deactivated, or otherwise disabled when associated with eggs 1 identified by the opacity identification system 600 as, for example, clear, early-dead, or missing. That is, eggs 1 that are clear, early-dead, or missing may undesirably allow significant amounts of transmitted light to reach the detector assembly 300. As such, the opacity identification system 600 may be in communication with the controller of the egg identification system 100 such that the controller may selectively direct operation of the emitter assembly 200 and/or the detector assembly 300 associated with the spectroscopy detector system 700. In this manner, detector saturation may be minimized by communicating to the controller that certain emitter-detector pairs should be disabled for a given egg flat 50.

According to some aspects, each egg may undergo evaluation and identification by more than one emitter-detector pair when passing through the spectroscopy detection system 700 to further ensure improved accuracy of the identification system.

According to some aspects, the emitter-detector pairs may subdivided into various subsets operating at varying wavelengths or different optical bandwidths to improve performance of the egg identification system 160. This may be regardless of whether the emitter-detector pairs are operating in a absorption spectroscopy mode or a fluorescence spectroscopy mode. For example, as shown in FIG. 10, the emitter-detector pairs forming the spectroscopy detection system 700 may be subdivided into subsets 710, 720, 730, with each subset operating at a different optical bandwidth such that each egg passing through the spectroscopy detection system 700 may be analyzed more than once and at varying optical bandwidths in determining its classification. It is understood that the number of emitter-detector pairs or subsets shown are for illustrative purposes only and that any number of emitter-detector pairs or subsets may be provided.

According to some aspects of the present disclosure, as shown in FIG. 11, the spectroscopy detection system 700 may include an absorption spectroscopy system 800 and a fluorescence spectroscopy system 900 that operate in an absorption spectroscopy mode and a fluorescence spectroscopy mode, respectively. In this regard, in addition to the opacity identification system 600, the egg detection system 160 may include the absorption spectroscopy system 800 and the fluorescence spectroscopy system 900 for improving identification accuracy.

In some instances, the emitter-detector pairs of the absorption spectroscopy system 800 and the fluorescence spectroscopy system 900 may subdivided into various subsets operating at varying wavelengths or different optical bandwidths to improve performance of the spectroscopy detection system 700. For example, as shown in FIG. 11, the emitter-detector pairs forming the absorption spectroscopy system 800 may be subdivided into subsets 810, 820, 830, with each subset operating at a different optical bandwidth such that each egg passing through the absorption spectroscopy system 800 may be analyzed more than once and at varying optical bandwidths in determining its classification. Further, the emitter-detector pairs forming the fluorescence spectroscopy system 900 may be subdivided into subsets 910, 920, with each subset operating at a different optical bandwidth such that each egg passing through the fluorescence spectroscopy system 900 may be analyzed more than once and at varying optical bandwidths in determining its classification It is understood that the number of emitter-detector pairs or subsets shown are for illustrative purposes only and that any number of emitter-detector pairs or subsets may be provided. In some instances, even within the subsets, the emitter-detector pairs may be configured to operate at differing wavelengths or optical bandwidths. While the absorption spectroscopy system 800 is illustrated upstream of the fluorescence spectroscopy system 900, the order may be reversed in some instances.

The systems and methods described herein may also be referred to as non-invasive in that egg shell structure remains intact throughout the evaluation of the egg. Furthermore, aspects of the present disclosure do not require substances to be introduced into the egg shell or the internal components of the egg in order to evaluate the egg for viability, although in some instances such substances, such as biomarkers, may be introduced prior to evaluation. Such aspects involving the introduction of one or more substances, however, would be considered invasive.

Many modifications and other aspects of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific aspects disclosed and that modifications and other aspects are intended to be included within the scope of the appended claims. Although specific terms are employed herein, they are used in a generic and descriptive sense only and not for purposes of limitation.

That which is claimed:

1. An egg identification system for determining viability of an avian egg, comprising:
    a conveyor system configured to convey an egg flat containing a plurality of eggs;
    an emitter assembly configured to emit electromagnetic radiation toward one of the eggs conveyed in the egg flat, the emitter assembly having a collimation lens to collimate the electromagnetic radiation emitted therefrom;
    a non-contact detector assembly axially aligned with the emitter assembly and having a spectrometer, the non-contact detector assembly being configured to detect the electromagnetic radiation transmitted through the egg, the non-contact detector assembly being disposed in a non-contact position such that the egg positioned for identification is spaced-apart from the non-contact detector assembly during operation thereof, the non-contact detector assembly having a light pipe comprising an optical filter and configured to reduce optical noise, and a collimation lens to collect the electromagnetic radiation transmitted through the egg within the field of view of the non-contact detector assembly; and
    a processor in communication with the spectrometer and configured to process an output signal of the non-contact detector assembly for determining whether the egg is viable, the processor being configured to generate a spectrum based on the output signal that represents light intensity as a function of wavelength, the processor being further configured to compare the generated spectrum with at least one spectrum associated with a known egg condition to identify a viability condition of the egg.

2. An egg identification system according to claim 1, wherein the spectrometer is configured to operate in one of infrared absorption spectroscopy mode and fluorescence spectroscopy mode.

3. An egg identification system according to claim 1, wherein the emitter assembly comprises a modulator configured to modulate the electromagnetic radiation emitted therefrom in the form of a modulated signal.

4. An egg identification system according to claim 1, wherein the emitter assembly and the non-contact detector assembly form an emitter-detector pair, and further wherein there are a plurality of the emitter-detector pairs divided into subsets, and further wherein a first subset of the emitter-detector pairs is configured to operate in an infrared absorption spectroscopy mode and a second subset of the emitter-detector pairs is configured to operate in a fluorescence spectroscopy mode such that each egg contained within the egg flat is subjected to both infrared absorption spectroscopy analysis and fluorescence spectroscopy analysis for determining viability of the eggs transported in the egg flat by the conveyor system.

5. An egg identification system according to claim 1, wherein the emitter assembly is configured to emit electromagnetic radiation at a wavelength different than that detected by the non-contact detector assembly.

6. An egg identification system according to claim 1, further comprising a plurality of the emitter assemblies being divided into subsets, wherein a first subset of the emitter assemblies is configured to emit electromagnetic radiation at a first wavelength and a second subset of the emitter assemblies is configured to emit electromagnetic radiation at a second wavelength different than the first wavelength.

7. An egg identification system according to claim 1, further comprising a plurality of the non-contact detector assemblies being divided into subsets, wherein a first subset of the non-contact detector assemblies is configured to detect electromagnetic radiation at a first optical bandwidth and a second subset of the non-contact detector assemblies is configured detect electromagnetic radiation at a second optical bandwidth.

8. A method of determining viability of an egg, the method comprising:
conveying an egg contained in an egg flat using a conveyor system;
emitting electromagnetic radiation from an emitter assembly toward the egg, the emitter assembly having a collimation lens to collimate the electromagnetic radiation emitted therefrom;
receiving electromagnetic radiation transmitted through the egg at a non-contact detector assembly axially aligned with the emitter assembly, the non-contact detector assembly being spaced-apart from the egg, and the non-contact detector assembly having a light pipe comprising an optical filter and configured to reduce optical noise, and a collimation lens to collect the electromagnetic radiation transmitted through the egg within the field of view of the non-contact detector assembly; and
processing an output signal of the non-contact detector assembly for determining whether the egg is viable, by generating a spectrum based on the output signal that represents light intensity as a function of wavelength, and comparing the generated spectrum with at least one spectrum associated with a known egg condition to identify a viability condition of the egg.

9. A method according to claim 8, wherein processing an output signal of the non-contact detector assembly comprises processing an output signal of the non-contact detector assembly in one of an infrared absorption spectroscopy mode and a transmission fluorescence spectroscopy mode.

10. A method according to claim 8, wherein emitting electromagnetic radiation from an emitter assembly comprises modulating the electromagnetic radiation emitted from the emitter assembly in the form of a modulated signal.

11. A method according to claim 8, further comprising providing a plurality of the emitter assemblies and the non-contact detector assemblies, each emitter assembly being associated with a respective non-contact detector assembly to form an emitter-detector pair, the emitter-detector pairs being divided into subsets, and wherein conveying the egg comprises conveying the egg past a first subset of the emitter-detector pairs implementing a transmission absorption spectroscopy mode and a second subset of the emitter-detector pairs implementing a transmission fluorescence spectroscopy mode such that the egg is subjected to both transmission absorption spectroscopy and transmission fluorescence spectroscopy for determining viability.

12. A method according to claim 8, wherein emitting electromagnetic radiation from an emitter assembly further comprises emitting electromagnetic radiation at a wavelength different than that detected by the non-contact detector assembly.

13. A method according to claim 8, further comprising providing a plurality of the emitter assemblies divided into subsets, and emitting electromagnetic radiation from a first subset of the emitter assemblies at a first wavelength and emitting electromagnetic radiation from a second subset of the emitter assemblies at a second wavelength different than the first wavelength.

14. A method according to claim 8, further comprising providing a plurality of the non-contact detector assemblies divided into subsets, and detecting electromagnetic radiation from a first subset of the non-contact detector assemblies at a first optical bandwidth and detecting electromagnetic radiation from a second subset of the non-contact detector assemblies at a second optical bandwidth.

* * * * *